United States Patent [19]

Langlois et al.

[11] 4,395,416
[45] Jul. 26, 1983

[54] 1-SPIRO ISOBENZOFURANIC AND 1-SPIRO ISOBENZOTHIOPHENIC DERIVATIVES THE PROCESS FOR PREPARING THE SAME AND THEIR USE IN THERAPEUTICS

[75] Inventors: Michel Langlois, Buc; Bernard P. Bucher, Marnes la Coquette; Philippe L. Dostert, Paris; Alain P. Lacour, La Varenne; Gerard H. Moinet, Orsay, all of France

[73] Assignee: Delalande S.A., Courbevoie, France

[21] Appl. No.: 341,415

[22] Filed: Jan. 21, 1982

[30] Foreign Application Priority Data

Jan. 29, 1981 [FR] France .................... 81 01692
Jan. 14, 1982 [FR] France .................... 81 00518

[51] Int. Cl.³ ............... A61K 31/395; C07D 491/07
[52] U.S. Cl. .................... 424/267; 424/274; 424/279; 546/17; 548/409; 548/411; 549/265
[58] Field of Search ............ 346/17; 548/409, 411; 424/267, 274, 279; 549/265

[56] References Cited

U.S. PATENT DOCUMENTS 3,980,787 9/1976 Klioze et al. ............... 546/17
4,263,817 4/1981 Martin et al. ............... 549/268

Primary Examiner—Robert T. Bond
Attorney, Agent, or Firm—Flynn, Thiel, Boutell & Tanis

[57] ABSTRACT

Derivatives of formula:

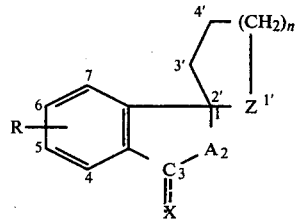

in which Z< represents:
  either an amino group of struture >N-$R_1$ where $R_1$ represents a linear or branched alkyl group with 1 to 5 carbon atoms or a phenyl group possibly substituted by a chlorine atom, in which case:
  n=1 or 2,
  the pair (A, C≡≡≡≡X) assumes the following values: (S, C=O), (S, $CH_2$), (O, $CH_2$), (O, CH—$C_6H_5$), and
  R represents a hydrogen or halogen atom, one or more methoxy groups or the butadiene-1,3 ylene chain

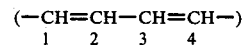

fixed in position 5,6 of the phenyhl nucleus and thus forming with this latter a naphthyl nucleus;
or a methylene group (—$CH_2$—), in which case:
  n=1 or 2,
  A represents the oxygen atom,
  >C≡≡≡≡X represents a carbonyl group (>C=O) or thiocarbonyl group (>C=S), and
  R has the same meanings as previously,
as well as the mineral or organic acid addition salts thereof. The compounds exhibit anti-convulsion and analgesic activity.

13 Claims, No Drawings

1-SPIRO ISOBENZOFURANIC AND 1-SPIRO ISOBENZOTHIOPHENIC DERIVATIVES THE PROCESS FOR PREPARING THE SAME AND THEIR USE IN THERAPEUTICS

The present invention relates to new spiro-1 isobenzofuranic and spiro-1 isobenzothiophenic derivatives, the process for preparing same and the application thereof in therapeutics.

The derivatives of the invention correspond more precisely to the general formula:

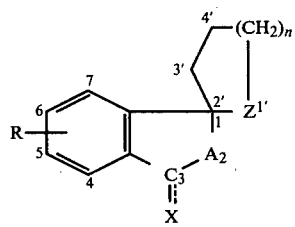
(I)

in which $Z<$ represents:
either an amino group of structure $>N-R_1$, where $R_1$ represents a linear or branched alkyl group having 1 to 5 carbon atoms or a phenyl group possibly substituted by a chlorine atom, in which case:
$n=1$ or 2,
the pair (A, C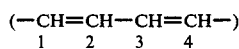X) assumes the following values (S, C=O), (S, CH$_2$), (O, CH$_2$), (O, CH—C$_6$H$_5$), and
R represents a hydrogen or halogen atom, one or more methoxy groups or the butadiene-1,3 ylene chain $$(-CH=CH-CH=CH-)$$
$$\quad\; 1 \quad\; 2 \quad\; 3 \quad\; 4$$

fixed in position 5,6 of the phenyl nucleus and thus forming with this latter, a naphthyl nucleus; or a methylene group (—CH$_2$—), in which case:
$n=1$ or 2,
A represents the oxygen atom,
$>$C========X represents a carbonyl group ($>$C=O) or a thiocarbonyl group ($>$C=S), and R has the same meanings as above.

Among the compounds of formula (I) of the invention, the following, in particular, may be mentioned:
those in which $Z<$ represents the amino group with structure $>N-R_1$ such as defined previously and the pair (A, C========X) assumes the value (S, C=O), (O, CH$_2$) or (S, CH$_2$), among which compounds those are preferred in which $R_1$ represents a methyl or ethyl group, R represents the hydrogen atom or a halogen atom in position 5 and n assumes those in which $Z<$ represents the methylene group (—CH$_2$—) and the pair (A, C========X) assumes the value (O, C=O) or (O, C=S).

The present invention also relates to the mineral or organic acid addition salts, preferably pharmaceutically acceptable, of the formula (I) compounds in which $Z<$ represents an amino group of structure $>N-R_1$.

The process for preparing the compounds of the invention having the particular formula:

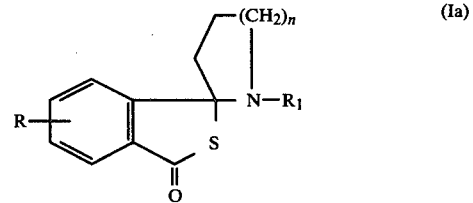
(Ia)

in which n, $R_1$, and R have the same meanings as in formula (I) consists in treating with phosphorous pentasulfide, in the presence of a basic agent such as triethylamine, pyridine or sodium bicarbonate for example, and preferably in solution in an aprotic organic solvent such as toluene or acetonitrile for example, and at ambient temperature, the compounds of formula:

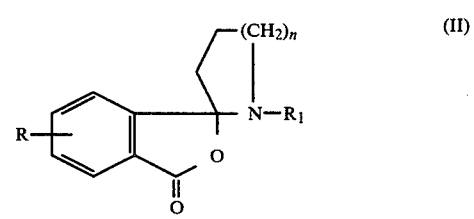
(II)

in which R, $R_1$ and n have the same meanings as in formula (Ia).

Compounds (II), for their part, are obtained:
either by treating with hydrochloric acid, preferably 3 N, at reflux, the compounds of formula:

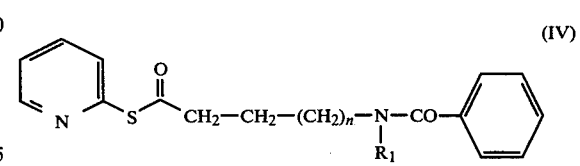
(III)

in which R, $R_1$ and n have the same meanings as in formula (II).

The formula (III) compounds, which are new, are obtained by condensation of the compounds of formula:

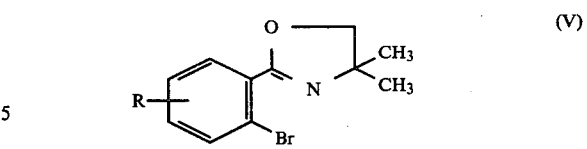
(IV)

in which n and $R_1$ have the same meanings as in formula (III), respectively with the magnesians of the compounds of formula:

(V)

in which R has the same meanings as in formula (III).

The compounds of formula (IV) are obtained by condensation in a dioxane medium and in the presence of dicyclohexylcarbodiimide (D.C.C.I.), of 2-mercaptopyridine and compounds of formula:

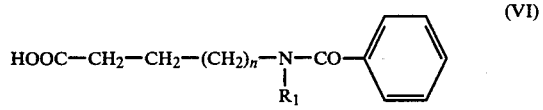
(VI)

in which $R_1$ and n have the same meanings as in formula (IV) and the compounds of formula (V) are obtained by using known methods and in particular those described in J. Med. Chem. 19, 1315 (1976); J.O.C. 40, 1427 (1975); and J.A.C.S. 92, 6646 (1970).

Similarly, the compounds of formula (VI) are obtained by using the method described in Chem. Ber. 95, 2424 (1962);

or by condensation of lithium derivatives of the compounds of formula:

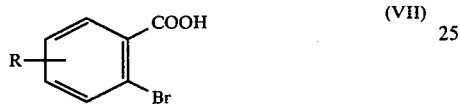
(VII)

in which R has the same meanings as in formula (II), respectively with the lactams of formula:

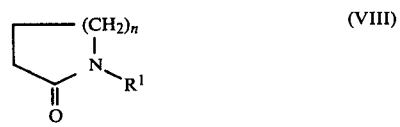
(VIII)

in which $R_1$ and n have the same meanings as in formula (II), this condensation being preferably carried out in tetrahydrofuran, at a temperature from $-100°$ C. to $-80°$ C. and with the help of a solution of butyl lithium in hexane.

The process for preparing the compounds of the invention of the particular formula:

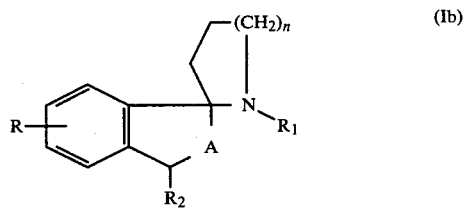
(Ib)

in which $R_1$, R and n have the same meanings as in formula (I) and the pair (A, $R_2$) assumes the value (S, H), (O, H) or (O, $C_6H_5$), consists in condensing the lithium derivatives of the compounds of formula:

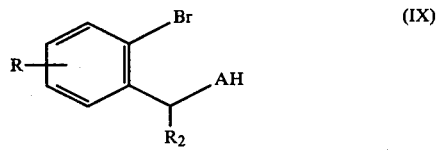
(IX)

in which R and the pair (A, $R_2$) have the same meanings as in formula (Ib), respectively with the compounds of formula (VIII).

The condensation is carried out according to the method described for preparing the compounds of formula (II) from the lithium derivatives of the compounds of formula (VII).

The compounds of formula (IX) are, for their part, prepared according to known methods described particularly in:

Chem. Ber. 113, 1304, (1980),
J.A.C.S. 100, 2779, (1978) and 78, 666, (1956),
J.O.C. 37, 1545, (1972), and
J. Med. Chem. 19, 1315, (1976).

Finally, the process for preparing the compounds of the invention having the particular formula:

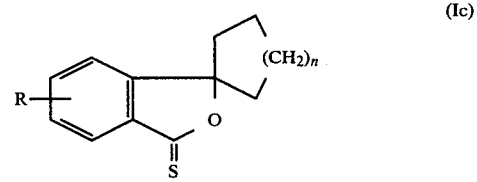
(Ic)

in which n and R have the same meanings as in formula (I), consists in treating to reflux preferably in toluene in the presence of phosphorous pentasulfide, the compounds of formula (I) having the particular structure:

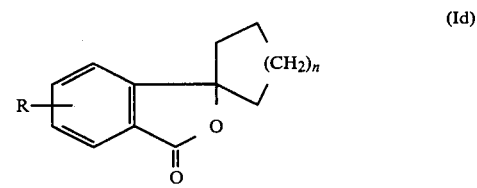
(Id)

in which n and R have the same meanings as in formula (Ic), the compounds of formula (Id) being obtained by condensation of the lithium derivatives of the compounds of formula (VII), respectively with the cyclanones of formula:

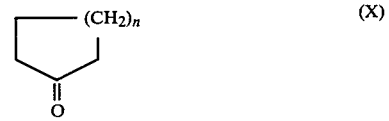
(X)

in which n=1 or 2, the condensation being carried out according to the above-described method for the synthesis of the compounds of formula (II) from the lithium derivatives of the compounds of formula (VII).

Moreover, the formula (I) compounds in which Z< represents the amino group of structure >N—$R_1$ may be salified according to the usual methods. Thus, salification may be achieved, for example, by action on these compounds of a mineral acid such as hydrochloric or hydrobromic acid or of an organic acid, preferably in an organic solvent.

The following preparations are given by way of examples to illustrate the invention.

EXAMPLE 1 spiro [isobenzothiophene-1 (3H) 2′-pyrrolidine]-one-3 ethyl-1′ (Ia)

Code number: 3

A suspension of 2 g of spiro [isobenzofuran-1 (3H) 2′-pyrrolidine]-one 3 ethyl-1′[(II), code number 12], and 1.3 g of phosphorous pentasulfide in 20 ml of acetonitrile and 6.5 ml of triethylamine is stirred for 12 hours at room temperature. Then it is thrown into a saturated sodium bicarbonate solution, extracted with chloroform, dried on sodium sulfate, filtered and the filtrate evaporated. The residue is chromatographed on a silica column. After elution with the petroleum ether (98%)—ethyl ether (2%) mixture, then crystallization in heptane, 1.6 g of the expected compound are obtained, some physico-chemical characteristics of which are given in Table I below.

By the same process, but from the corresponding reagents, the compounds of formula (I) are obtained which appear in table I under the code numbers 1, 2, 4 to 10, 16, 29 and 31 to 42.

EXAMPLE 2 spiro [isobenzofuran-1 (3H) 2′-pyrrolidine]-one-3 ethyl-1′, hydrate (II)

Code number: 12

1st step: (N-ethyl, N-benzoyl) amino-4 (pyridinyl-2) thio-1 butanone-1 [(IV), n=1, $R_1$=Et]

A suspension of 28.2 g of (N-ethyl, N-benzoyl) γ-amino butyric acid [(VI), n=1, $R_1$=Et], 13.3 g of 2-mercapto-pyridine and 24.7 g of D.C.C.I. in 300 ml of dioxane is left under agitation for 12 hours at room temperature. Then it is filtered and the filtrate evaporated under vacuum at 20° C. 34.4 g of the expected compound are obtained (Yield ~100%).

By the same process, but from the corresponding reagents, the compounds of formula (IV) are obtained in which n and $R_1$ have the above-defined values.

2nd step: [(dimethyl-4,4 dihydro-4,5 oxazolyl-2)-2 phenyl]-1 (N-ethyl N-benzoylamino)-4 butanone-1 [(III), R=H, n=1, $R_1$=Et]

To a suspension of 3.2 g of magnesium and an iodine crystal in the minimum of T.H.F., under an argon stream, there is added a solution of 29.3 g or ortho-bromophenyl-2 dimethyl-4,4 dihydro-4,5 oxazolidine [(V), R=H] in 250 ml of T.H.F. and it is brought up to reflux. The magnesian obtained is slowly added to a solution cooled to −40° C. of 39.4 g of the compound of formula (IV) obtained in the previous step (n=1, $R_1$=Et) in 250 ml of T.H.F. Then it is left to return to room temperature, the solvent is evaporated, the residue taken up in 2 N hydrochloric acid, washed with chloroform, neutralized with sodium carbonate, extracted with chloroform, dried on sodium sulfate, filtered, the filtrate is evaporated and the residue chromatographed on a silica column. After elution with the ethyl acetate (50%)-cyclohexane (50%) mixture, 17.6 g of the expected oily product are obtained.

Yield: 38%

NMR spectrum (CDCl$_3$) δppm: 7.8, m and 7.35, m: 9 aromatic H; 4.0, s: —CH$_2$—O—; 3.40, q, J=7 Hz:

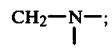

1.35, s: 2 CH$_3$; 1.20, t, J=7 Hz:

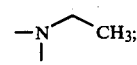

3.45, m, 2.78, m and 2.0, m; (—CH$_2$—CH$_2$—CH$_2$—).

By the same process, but from the corresponding reagents, the other compounds of formula (III) are obtained, which are required for the synthesis of formula (II) compounds and particularly:

[(dimethyl-4,4 dihydro-4,5 oxazolyl-2)-2 phenyl]-1 (N-methyl N-benzoylamino)-4 butanone-1 [(III), R=H, n=1, $R_1$=CH$_3$], whose NMR spectrum (CDCl$_3$) is as follows:

δppm=7.8 and 7.25, m: 9 aromatic H; 4.05, s: —CH$_2$—O—; 3.02, s:

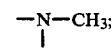

3.50, m, 2.70, m and 2.0, m: (—CH$_2$—CH$_2$—CH$_2$—); and

[(dimethyl-4,4 dihydro-4,5 oxazolyl-2)-2 methoxy-4 phenyl]-1 (N-methyl N-benzoylamino)-4 butanone-1 [(III), R=4-Meo, n=1, $R_1$=CH$_3$] whose NMR spectrum (CDCl$_3$) is as follows:

δppm=7.35, m: 8 aromatic H; 4.0, s: —CH$_2$—O—; 3.82, s: CH$_3$O—; 3.0, s: CH$_3$—N; 1.34, s: 2—CH$_3$; 3.50, m, 2.8, m and 2.0, m: (—CH$_2$—CH$_2$—CH$_2$).

3rd step: spiro [isobenzofuran-1 (3H) 2′-pyrrolidine] one-3 ethyl-1′, hydrate (II)

Code number: 12

A solution of 15.8 g of the compound obtained in the previous step [(III), R=H, n=1, $R_1$=Et], in 20 ml of concentrated hydrochloric acid, 20 ml of water and 8 ml of dimethoxyethane is brought to reflux for 48 hours. Then the dimethoxyethane is evaporated, the residue is washed with ether, basified with sodium bicarbonate and extracted with chloroform. It is dried on sodium sulfate, filtered, the filtrate is evaporated and the residue chromatographed on a silica column. After elution with chloroform then a chloroform (98%)—methanol (2%) mixture, 2.5 g of the expected product are obtained, some characteristics of which are shown in Table II below.

By the same process, but from the corresponding reagents, the formula (II) compounds are obtained appearing in table II under code numbers: 11, 13 to 15, 17 to 19, 25, 28, 30 and 46 to 56.

EXAMPLE 3 spiro [isobenzofuran-1 (3H) 2′-pyrrolidine] one-3 ethyl-1′, hydrate (II)

Code number: 12

To a solution cooled to −100° C. of 2-bromobenzoic acid (VII) in 600 ml of T.H.F. there is slowly added, while keeping the temperature at −100° C., 375 ml of a solution of 1.6 N of n-butyl-lithium in hexane. Then it is left under agitation for an hour at −100° C., the temperature is allowed to rise to −80° C. and 34 ml of N-ethyl-pyrrolidinone [(VIII), $R_1$=Et, n=1] are added in 30 minutes. It is left for two hours at −80° C. and the solution is thrown into 500 ml of 1.5 N hydrochloric acid and the benzoic acid formed is extracted with ether. Then the aqueous phase is neutralized by means of concentrated NaOH and extracted continuously for 48 hours by means of methylene chloride. Then the organic phase is evaporated and the residue crystallized in n-heptane. 10 g (Yield: 16%) of a compound identical to the one obtained in the third step of example 2 above, are obtained.

By the same process, but from the corresponding reagents, the compounds of formula (II) are obtained, shown in table II under code numbers: 11, 13 to 15, 17 to 19, 25, 28, 30 and 46 to 56, as well as:
the compounds of formula (I) having the particular structure (Ib) and code numbers: 21, 22 and 43 to 45, these latter being obtained from the formula (IX) and formula (VIII) compounds; and
the formula (I) compound having the particular structure (Id) shown under code number 23 obtained from the formula (VII) and formula (X) compounds; compounds 21 to 23 and 43 to 45 appearing in table I below.

EXAMPLE 4 spiro [cyclopentane-1 (3H) isobenzofuran]-thione-3 (Ic)

Code number: 24

A suspension of 4.1 g of spiro [cyclopentane-1 (3H) isobenzofuran]-one-3 (Id) and 5 g of phosphorous pentasulfide in 10 ml of toluene is brought to 80° C. for 12 hours. Then the solvent is evaporated and the residue chromatographed on a silica column. After elution with a heptane (85%)—ethyl acetate (15%) mixture, 3 g of the expected product are obtained some of whose physico-chemical properties appear in table I.

TABLE I

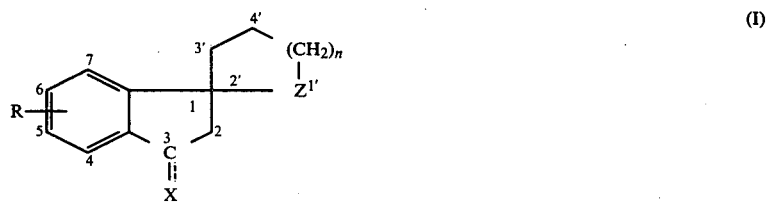

(I)

| Code Number | C X | A Z | R | $n$ | Form | Empirical formula | Molecular weight | Melting or boiling point (°C.) | ELEMENTARY ANALYSES or NRM Spectrum |  |  |
|---|---|---|---|---|---|---|---|---|---|---|---|
|  |  |  |  |  |  |  |  |  | % C | H | N |
| 1 | C=O | S  N—CH$_3$ | H | 1 | HCl | C$_{12}$H$_{14}$ClNOS | 255.76 | 146 | Cal. 56.35 | 5.52 | 5.48 |
|  |  |  |  |  |  |  |  |  | Obt. 56.34 | 5.61 | 5.31 |
| 2 | " | " " | " | 2 | Base | C$_{13}$H$_{15}$NOS | 233.32 | 97 | Cal. 66.92 | 6.48 | 6.00 |
|  |  |  |  |  |  |  |  |  | Obt. 67.02 | 6.67 | 6.08 |
| 3 | " | " N—Et | " | 1 | " | C$_{13}$H$_{15}$NOS | " | 80 | Cal. 66.92 | 6.48 | 6.00 |
|  |  |  |  |  |  |  |  |  | Obt. 66.97 | 6.77 | 5.98 |
| 4 | " | " N—C$_3$H$_{7n}$ | " | " | " | C$_{14}$H$_{17}$NOS | 247.35 | Oil | Cal. 67.98 | 6.93 | 5.66 |
|  |  |  |  |  |  |  |  |  | Obt. 67.82 | 6.99 | 5.97 |
| 5 | " | S  N—CH$_3$ | 6-Cl | " | Base | C$_{12}$H$_{12}$ClNOS | 253.75 | 74 | Cal. 56.80 | 4.77 | 5.52 |
|  |  |  |  |  |  |  |  |  | Obt. 57.04 | 4.78 | 5.54 |
| 6 | " | " " | 5-Cl | " | " | " | " | 95 | Cal. 56.80 | 4.77 | 5.52 |
|  |  |  |  |  |  |  |  |  | Obt. 56.67 | 4.97 | 5.50 |
| 7 | " | " N—Et | " | " | " | C$_{13}$H$_{14}$ClNOS | 267.77 | 127 | Cal. 58.31 | 5.27 | 5.23 |
|  |  |  |  |  |  |  |  |  | Obt. 58.17 | 5.21 | 4.96 |
| 8 | " | " N—CH$_3$ | 6-MeO | " | " | C$_{13}$H$_{15}$NO$_2$S | 249.32 | 103 | Cal. 62.62 | 6.06 | 5.62 |
|  |  |  |  |  |  |  |  |  | Obt. 62.22 | 5.90 | 5.61 |
| 9 | " | " " | 5-MeO | " | " | " | " | 113 | Cal. 62.62 | 6.06 | 5.62 |
|  |  |  |  |  |  |  |  |  | Obt. 62.58 | 6.01 | 5.36 |
| 10 | " | " " | 5,6-di MeO | " | " | C$_{14}$H$_{17}$NO$_3$S | 279.35 | 107 | Cal. 60.19 | 6.13 | 5.01 |
|  |  |  |  |  |  |  |  |  | Obt. 60.32 | 6.19 | 5.00 |
| 16 | " | " " | 5-F | " | " | C$_{12}$H$_{12}$FNOS | 237.29 | 109 | Cal. 60.74 | 5.10 | 5.90 |
|  |  |  |  |  |  |  |  |  | Obt. 60.91 | 5.16 | 6.18 |
| 21 | CH$_2$ | O " | H | " | " | C$_{12}$H$_{15}$NO | 189.25 | Bp$_{1.5}$= 70° C. | Cal. 76.15 | 7.99 | 7.40 |
|  |  |  |  |  |  |  |  |  | Obt. 76.05 | 8.10 | 7.50 |
| 22 | " | S " | " | " | " | C$_{12}$H$_{15}$NS | 205.31 | Oil | Cal. 70.19 | 7.36 | 6.82 |
|  |  |  |  |  |  |  |  |  | Obt. 70.40 | 7.47 | 6.77 |
| 23 | C=O | O  CH$_2$ | " | " | — | C$_{12}$H$_{12}$O$_2$ | 188.22 | 75 | Cal. 76.57 | 6.43 | — |
|  |  |  |  |  |  |  |  |  | Obt. 76.87 | 6.65 | — |
| 24 | C=S | " " | " | " | — | C$_{12}$H$_{12}$OS | 204.28 | Bp$_{0.2}$= 80° C. | Cal. 70.55 | 5.92 | — |
|  |  |  |  |  |  |  |  |  | Obt. 70.74 | 5.90 | — |
| 29 | C=O | S  N—CH$_3$ | 6-F | " | " | C$_{12}$H$_{12}$NFOS | 237.29 | 105 | Cal. 60.74 | 5.10 | 5.90 |
|  |  |  |  |  |  |  |  |  | Obt. 60.91 | 5.16 | 6.18 |

TABLE I-continued

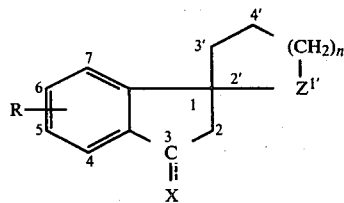

(I)

| Code Number | C | X | A | Z | R | η | Form | Empirical formula | Molecular weight | Melting or boiling point (°C.) | ELEMENTARY ANALYSES or NRM Spectrum % C H N |
|---|---|---|---|---|---|---|---|---|---|---|---|
| 31 | " | " | | N(CH₃)(CH₃) (isopropyl) | H | " | " | C₁₄H₁₇NOS | 247.35 | Oil | NMR Spectrum (CDCl₃)δ ppm=7.45, m, 4 aromatic H; between 3.4 and 1.95, m, 7H(cyclic —CH₂—CH₂—CH₂— and H CH₃ / N—CH(CH₃); 0.85 and 1.05, d, (J=7Hz): (—CH(CH₃)₂) |
| 32 | " | " | | N—CH₃ | 5-Cl | 2 | " | C₁₃H₁₄ClNOS | 267.77 | 72 | Cal. 58.31 5.27 5.23 Obt. 58.18 5.44 5.39 |
| 33 | " | " | | " | 4-Cl | 1 | " | C₁₂H₁₂ClNOS | 253.75 | 101 | Cal. 56.80 4.77 5.52 Obt. 56.62 4.57 5.22 |
| 34 | " | " | | N—C₃H₇ₙ | 5-Cl | " | " | C₁₄H₁₆ClNOS | 281.80 | 86 | Cal. 59.67 5.73 4.97 Obt. 59.37 6.03 5.26 |
| 35 | " | " | | N—C₄H₉ₙ | " | " | HBr | C₁₅H₁₉BrClNOS | 376.74 | 140 | Cal. 47.82 5.08 3.72 Obt. 47.79 5.26 3.44 |
| 36 | " | " | | N-isobutyl | " | " | HCl | C₁₅H₁₉Cl₂NOS | 332.29 | 86 | Cal. 54.22 5.76 4.22 Obt. 54.64 5.93 4.36 |
| 37 | " | " | | N—C₆H₅ | H | " | Base | C₁₇H₁₅NOS | 281.36 | 165 | Cal. 72.56 5.37 4.98 Obt. 72.14 5.61 5.04 |
| 38 | " | " | | " | 5-Cl | " | " | C₁₇H₁₄ClNOS | 315.81 | 257 | Cal. 64.65 4.47 4.44 Obt. 64.52 4.43 4.16 |
| 39 | " | " | | N—C₆H₄—Cl | H | " | " | C₁₇H₁₄ClNOS | " | 164 | Cal. 64.65 4.47 4.44 Obt. 64.73 4.53 4.35 |
| 40 | " | " | | " | 5-Cl | " | " | C₁₇H₁₃Cl₂NOS | 350.26 | 210 | Cal. 58.29 3.74 4.00 Obt. 57.99 3.58 3.77 |
| 41 | " | " | | N—CH₃ | 5-Br | " | " | C₁₂H₁₂BrNOS | 298.20 | 86 | Cal. 48.33 4.06 4.70 Obt. 48.26 3.98 4.82 |
| 42 | " | " | | " | 5,6-benzo | " | " | C₁₆H₁₅NOS | 269.35 | 65 | Cal. 71.34 5.61 5.20 Obt. 71.04 5.57 5.09 |
| 43 | CH₂ | O | | " | 5-Cl | " | " | C₁₂H₁₄ClNO | 223.70 | Bp₀.₀₅=108 | Cal. 64.43 6.31 6.26 Obt. 64.72 6.65 5.93 |
| 44 | CH—C₆H₅ | O | | N—CH₃ | H | " | " | C₁₈H₁₉NO | 265.34 | 71 | Cal. 81.47 7.22 5.28 Obt. 81.53 7.37 5.11 |
| 45 | CH₂ | S | | " | 5-Cl | " | " | C₁₂H₁₄ClNS | 239.76 | Oil | Cal. 60.11 5.89 5.84 Obt. 60.41 5.88 5.95 |

TABLE II

(II)

| Code Number | N—R₁ | R | n | Form | Empirical formula | Molecular weight | Melting point (°C.) | | ELEMENTARY ANALYSIS or NMR Spectrum | | |
|---|---|---|---|---|---|---|---|---|---|---|---|
| | | | | | | | | % | C | H | N |
| 11 | N—CH₃ | H | 2 | Base | $C_{13}H_{15}NO_2$ | 217.26 | 93 | Cal. | 71.86 | 6.96 | 6.45 |
| | | | | | | | | Obt. | 71.62 | 7.10 | 6.35 |
| 12 | N—Et | H | 1 | Hydrated base | $C_{13}H_{15}NO_2 +$ 1.1 $H_2O$ | 237.06 | 64 | Cal. | 65.75 | 7.32 | 5.90 |
| | | | | | | | | Obt. | 65.47 | 7.11 | 5.94 |
| 13 | N—$C_3H_{7n}$ | " | " | Sulfate | $C_{14}H_{19}NO_6S$ | 329.37 | 126 | Cal. | 51.05 | 5.81 | 4.25 |
| | | | | | | | | Obt. | 50.76 | 5.83 | 4.24 |
| 14 | N—CH₃ | 6-Cl | " | " | $C_{12}H_{14}ClNO_6S$ | 335.76 | 180 | Cal. | 42.92 | 4.20 | 4.17 |
| | | | | | | | | Obt. | 42.85 | 4.16 | 4.30 |
| 15 | " | 5-Cl | " | " | " | " | 179 | Cal. | 42.92 | 4.20 | 4.17 |
| | | | | | | | | Obt. | 42.85 | 4.11 | 4.15 |
| 17 | " | 6-MeO | " | Hydrated base | $C_{13}H_{15}NO_3 +$ ½ $H_2O$ | 239.26 | 90 | Cal. | 65.25 | 6.60 | 5.85 |
| | | | | | | | | Obt. | 65.06 | 6.42 | 5.82 |
| 18 | " | 5-MeO | " | Base | $C_{13}H_{15}NO_3$ | 233.26 | 120 | Cal. | 66.93 | 6.48 | 6.01 |
| | | | | | | | | Obt. | 67.14 | 6.48 | 5.94 |
| 19 | " | 5,6-di MeO | " | " | $C_{14}H_{17}NO_4$ | 263.28 | 139 | Cal. | 63.86 | 6.51 | 5.32 |
| | | | | | | | | Obt. | 63.66 | 6.68 | 5.30 |
| 25 | " | 5-F | " | " | $C_{12}H_{12}FNO_2$ | 221.22 | 95 | NMR Spectrum (CDCl₃)δ ppm = 7.42, m, 3 aromatic H; 3.20, m and 2.22, m, (cyclic —CH₂—CH₂—CH₂—); 2.18, s, CH₃—N. | | | |
| 28 | " | 6-F | " | " | $C_{12}H_{12}FNO_2$ | 221.22 | 95 | Cal. | 65.15 | 5.47 | 6.33 |
| | | | | | | | | Obt. | 65.00 | 5.78 | 6.18 |
| 30 |  | H | " | Hydrated base | $C_{14}H_{17}NO_2 +$ 1.2 $H_2O$ | 252.84 | 65 | Cal. | 66.50 | 7.72 | 5.54 |
| | | | | | | | | Obt. | 66.60 | 7.69 | 5.80 |
| 46 | N—CH₃ | 5-Cl | 2 | Base | $C_{13}H_{14}ClNO_2$ | 251.71 | 103 | NMR Spectrum (CDCl₃)δ ppm= from 7.35 to 7.82, m (3 aromatic H); 2.96, m (CH₂ at 3'); 2,s (CH₃); 1.98,m (CH₂ at 4', 5'and 6') | | | |
| 47 | " | 4-Cl | 1 | " | $C_{12}H_{12}ClNO_2$ | 237.68 | 120 | Cal. | 60.64 | 5.09 | 5.89 |
| | | | | | | | | Obt. | 60.12 | 5.07 | 5.69 |
| 48 | N—$C_3H_{7n}$ | 5-Cl | " | " | $C_{14}H_{16}ClNO_2$ | 265.73 | Oil | NMR Spectrum (CDCl₃)δ ppm = 7.22 to 7.8, m (3H aromatic); 3.25, m (CH₂ at 3'); 2.30, m (CH₂N and CH₂ in 4' and 5'); 1.32, 9 and 0.72, t (CH₂—CH₃) | | | |
| 49 | N—$C_4H_{9n}$ | " | " | " | $C_{15}H_{18}ClNO_2$ | 279.76 | " | NMR Spectrum (CDCl₃)δ ppm = 7.3 to 7.9, m (3 aromatic H); 3.3, m (CH₂ at 3'); 2.3, m (CH₂—N and CH₂ at 4' and 5'); 1.32, m and 0.85, m (CH₂—CH₂—CH₃) | | | |
| 50 | 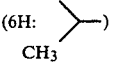 | " | " | " | $C_{15}H_{18}ClNO_2$ | 279.76 | Oil | NMR Spectrum (CDCl₃)δ ppm =7.2 to 7.8, m (3 aromatic H); 3.2, m (CH₂ at 3'); from 1.7 to 2.5, m (7H:CH₂ in 4' and 5', CH₂N and C—H); 0.68, d (6H: (CH₃)₂CH—) | | | |
| 51 |  | H | " | " | $C_{17}H_{15}NO_2$ | 265.30 | 164 | Cal. | 76.96 | 5.70 | 5.28 |
| | | | | | | | | Obt. | 77.18 | 5.95 | 5.35 |
| 52 | " | 5-Cl | " | " | $C_{17}H_{14}ClNO_2$ | 299.75 | 186 | Cal. | 68.11 | 4.71 | 4.67 |
| | | | | | | | | Obt. | 68.30 | 4.67 | 4.52 |
| 53 |  | H | " | " | " | " | 203 | Cal. | 68.11 | 4.71 | 4.67 |
| | | | | | | | | Obt. | 67.88 | 4.71 | 4.47 |
| 54 | " | 5-Cl | " | " | $C_{17}H_{13}Cl_2NO_2$ | 334.19 | 200 | Cal. | 61.09 | 3.92 | 4.19 |
| | | | | | | | | Obt. | 61.22 | 4.04 | 4.36 |

TABLE II-continued

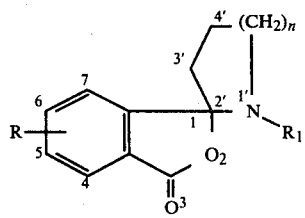

(II)

| Code Number | N—$R_1$ | R | n | Form | Empirical formula | Molecular weight | Melting point (°C.) | ELEMENTARY ANALYSIS or NMR Spectrum | | | |
|---|---|---|---|---|---|---|---|---|---|---|---|
| | | | | | | | | % | C | H | N |
| 55 | N—$CH_3$ | 5-Br | '' | '' | $C_{12}H_{12}BrNO_2$ | 283.14 | 126 | NMR Spectrum ($CDCl_3$)δ ppm = 7.2 to 8 (3 aromatic $H^3$); 3.22, m ($CH_2$ in 3'); 2.18, s ($CH_3$); 2.30, m ($CH_2$ in 4' and 5') | | | |
| 56 | '' | 5,6-  | '' | '' | $C_{16}H_{15}NO_2$ | 253.29 | 97 | Cal. Obt. | 75.87 75.13 | 5.97 5.92 | 5.53 5.60 |

The compounds of formula (I) and the salts thereof were tested on laboratory animals and showed pharmacological activities, especially in the field of the central nervous system, and in particular anti-convulsion and analgesic properties.

The anti-convulsion activity was revealed in mice by the test of protection against death induced by an intravenous injection of 0.7 mg/kg of bicuculline according to the method described by PEREZ de la MORA in Biochem. Pharmacol. 22, 2635 (1973).

The analgesic activity was shown up on mice by interperitoneal injection of the compounds of formula (I) and their salts using the phenylbenzoquinone test according to the method described by E. SIEGMUND in Proced. Soc. Exp. Biol. and Med. 95, 729 (1957).

To illustrate the invention, some results obtained in the above tests with the formula (I) compounds and salts thereof are shown in table III below.

TABLE III

| Code Number of compounds tested | Acute toxicity (mice - LD 50) (mg/kg/i.p.) | Efficient doses 50 - ED 50) protecting against death induced by Bicuculline (mg/kg/i.p.) | Phenylbenzoquinone test - ED 50 (mg/kg/i.p.) |
|---|---|---|---|
| 1 | 400 | 7 | 30 |
| 2 | >400 | 100 | 50 |
| 3 | >400 | 26 | |
| 4 | >400 | 47 | 35 |
| 5 | >400 | 80 | |
| 6 | >400 | 8 | |
| 7 | >400 | 10 | |
| 8 | >400 | 100 | |
| 9 | >400 | 40 | |
| 10 | >400 | 30 | |
| 21 | 275 | 15 | 100 |
| 22 | 290 | 34 | |
| 23 | >400 | 76 | |
| 24 | >400 | 63 | 46 |
| 16 | >400 | 25 | |
| 34 | 40% at 400 | 11 | |
| 35 | 60% at 400 | 26 | |
| 36 | >400 | 30 | |
| 37 | '' | 100 | |
| 38 | '' | 56 | |
| 39 | '' | 62 | |
| 40 | '' | 100 | |
| 41 | '' | 29.5 | |
| 42 | '' | 34 | |
| 43 | '' | 27.5 | 30 |
| 44 | '' | 45 | 64 |

TABLE III-continued

| Code Number of compounds tested | Acute toxicity (mice - LD 50) (mg/kg/i.p.) | Efficient doses 50 - ED 50) protecting against death induced by Bicuculline (mg/kg/i.p.) | Phenylbenzoquinone test - ED 50 (mg/kg/i.p.) |
|---|---|---|---|
| 45 | '' | 15 | |

The difference between lethal and active doses permits the compounds of formula (I) and the salts thereof to be used in therapeutic, especially in the treatment of troubles of the central nervous system (in particular as anti-convulsion and analgesic agents).

The present invention further relates to pharmaceutical compositions containing, as active ingredient, at least one of the compounds of formula (I) and the salts thereof, in association with a pharmaceutically accepted vehicle. Thus, for example, these compositions will be administered orally in the form of tablets, pills or capsules, in an amount up to 1 g per day, taken in one or several doses, or intravenously or intramuscularly, in the form of injectable ampoules in an amount up to 100 mg/day, in one or more injections.

We claim:

1. A compound of the formula

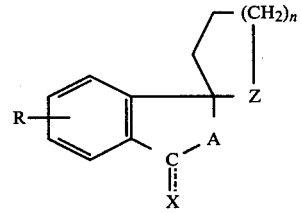

in which Z is >N—$R_1$ or —$CH_2$—, wherein $R_1$ is alkyl having 1 to 5 carbon atoms, phenyl or chlorophenyl, and in which 1. when
   Z is >N—$R_1$,
   n is 1 or 2,
   the pair (A,>C$\text{=======}$X) is selected from the group consisting of (S, C=O), (S, $CH_2$), (O, $CH_2$) and (O, CH—$C_6H_5$), and R is hydrogen, halogen, one or two methoxy groups or —CH=CH—CH=CH— connected to the 5 and 6 positions of the phenyl nucleus whereby to form a naphthyl nucleus, and 2. when Z is —CH$_2$—
n is 1 or 2
A is oxygen,
>C======X is >C=O or >C=S, and
R is the same as defined above, with the provisos that
(a) when >C======X is >C=O, R is not hydrogen, and
(b) when the pair (>C======X, n) is (>C=O, 2), R is not 5—Br, and the pharmacologically acceptable acid addition salts thereof when Z is >N—R$_1$.

2. A compound as claimed in claim 1 in which Z is >N—R$_1$, A is sulfur and >C======X is >C=O.

3. A compound as claimed in claim 2, wherein the set (n, R, Z) is selected from the group consisting of:
(1, H, NCH$_3$), (2, H, NCH$_3$), (1, H, NEt), (1, H, NC$_3$H$_{7n}$),
(1, 6—Cl, NCH$_3$), (1, 5—Cl, NCH$_3$), (1, 5—Cl, NEt), (1, 6—CH$_3$O, NCH$_3$),
(1, 5—CH$_3$O, NCH$_3$), (1, 5,6-diCH$_3$O, NCH$_3$), (1, 5—F, NCH$_3$),
(1, 6—F, NCH$_3$), (1, H, N<), (2, 5—Cl, NCH$_3$), (1, 4—Cl, NCH$_3$), (1, 5-Cl, NC$_3$H$_{7n}$), (1, 5-Cl, NC$_4$H$_{9n}$), (1, 5-Cl, N⌐⌐), (1, H, NC$_6$H$_5$), (1, 5-Cl, NC$_6$H$_5$), (1, H, N—⌬—Cl), (1, 5-Cl, N—⌬—Cl), (1, 5-Br, NCH$_3$) and (1, 5,6-CH=CH—CH=CH—, NCH$_3$).

4. A compound as claimed in claim 1 in which Z is —CH$_2$—.

5. A compound as claimed in claim 4 in which >C======X is >C=S, n is 1 and R is hydrogen.

6. A compound as claimed in claim 1 in which Z is >N—R$_1$, and the pair (A, >C======X) is selected from the group consisting of (S, >CH$_2$), (O, >CH$_2$) and (O, >CH—C$_6$H$_5$).

7. A compound as claimed in claim 6 in which the set (Z, n, R) is selected from the group consisting of (NCH$_3$, 1, hydrogen) and (NCH$_3$, 1, 5—Cl).

8. A compound of the formula

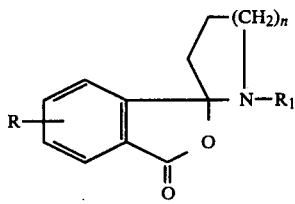

wherein n is 1 or 2, R$_1$ is alkyl having 1 to 5 carbon atoms, phenyl or chlorophenyl, and R is hydrogen, halogen, one or two methoxy groups or —CH=CH—CH=CH— connected to the 5 and 6 positions of the phenyl nucleus whereby to form a naphthyl nucleus.

9. A process for preparing a compound of the formula

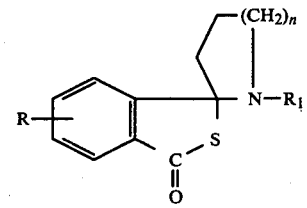

in which R$_1$ is alkyl having 1 to 5 carbon atoms, phenyl or chlorophenyl, n is 1 or 2, and R is hydrogen, halogen, one or two methoxy groups or —CH=CH—CH=CH— connected to the 5 and 6 positions of the phenyl nucleus whereby to form a naphthyl nucleus, which comprises reacting a compound of the formula

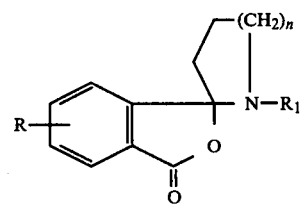

with phosphorus pentasulfide, in the presence of a base.

10. A process for preparing a compound of the formula

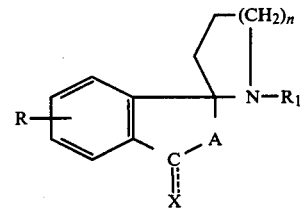

in which the pair (C======X, A) is selected from the group consisting of (CH$_2$, O), (CH—C$_6$H$_5$, O) and (CH$_2$, S), R$_1$ is alkyl having 1 to 5 carbon atoms, phenyl or chlorophenyl, n is 1 or 2, and R is hydrogen, halogen, one or two methoxy groups or —CH=CH—CH=CH— connected to the 5 and 6 positions of the phenyl nucleus whereby to form a naphthyl nucleus, which comprises condensing the lithium derivative of a compound of the formula

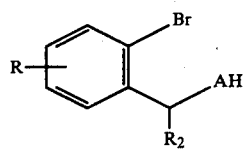

in which R has the same meaning as defined above, and the pair (A, R$_2$) is selected from the group consisting of (S, H), (O, H) and (O, C$_6$H$_5$), with a compound of the formula

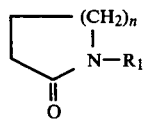

in which $R_1$ and n have the same meanings as defined above.

11. A process for preparing a compound of the formula

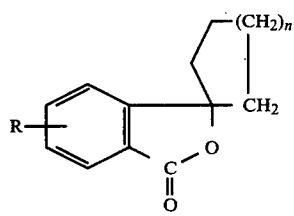

in which n is 1 or 2, and R is hydrogen, halogen, one or two methoxy groups, or —CH=CH—CH=CH— connected to the 5 and 6 positions of the phenyl nucleus whereby to form a naphthyl nucleus, which comprises condensing the lithium derivative of a compound of the formula

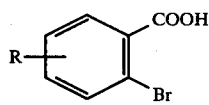

in which R has the same meaning as defined above, with a compound of the formula

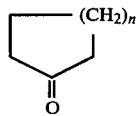

12. A process for preparing a compound of the formula

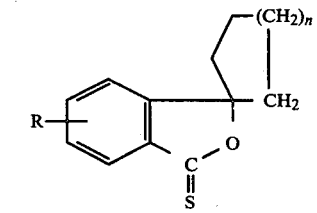

in which n is 1 or 2, and R is hydrogen, halogen, one or two methoxy groups, or —CH=CH—CH=CH— connected to the 5 and 6 positions of the phenyl nucleus whereby to form a naphthyl nucleus, which comprises reacting a compound of the formula

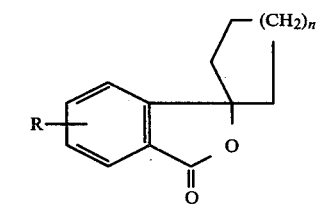

in which n and R have the same meanings as defined above, with phosphorus pentasulfide.

13. An analgesic or anticonvulsant composition comprising a therapeutically effective amount of a compound of the formula

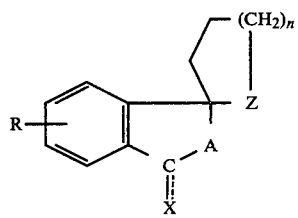

in which Z is >N—$R_1$ or —$CH_2$—, wherein $R_1$ is alkyl having 1 to 5 carbon atoms, phenyl or chlorophenyl, and in which
1. when
   Z is >N—$R_1$,
   n is 1, or 2,
   the pair (A, >C═══X) is selected from the group consisting of (S, C=O), (S, $CH_2$), (O, $CH_2$) and (O, CH—$C_6H_5$), and
   R is hydrogen, halogen, one or two methoxy groups or —CH=CH—CH=CH— connected to the 5 and 6 positions of the phenyl nucleus whereby to form a naphthyl nucleus, and
2. when
   Z is —$CH_2$—
   n is 1 or 2,
   A is oxygen,
   >C═══X is >C=O or >C=S, and
   R is the same as defined above,
and the pharmacologically acceptable acid addition salts thereof when Z is >N—$R_1$, in combination with a pharmaceutically acceptable vehicle.

* * * * *